United States Patent [19]

Cantatore

[11] Patent Number: 4,696,961
[45] Date of Patent: Sep. 29, 1987

[54] POLYMERIC COMPOUNDS CONTAINING PIPERIDINE RADICALS AND THEIR USE AS STABILIZERS FOR SYNTHETIC POLYMERS

[75] Inventor: Giuseppe Cantatore, Bitonto, Italy

[73] Assignee: Ciba-Geigy Corporation, Ardsley, N.Y.

[21] Appl. No.: 652,631

[22] Filed: Sep. 20, 1984

[30] Foreign Application Priority Data

Sep. 23, 1983 [IT] Italy ................ 22976 A/83

[51] Int. Cl.$^4$ ................ C08K 5/34; C08F 283/00
[52] U.S. Cl. ................ 524/100; 524/516; 524/521; 525/186; 525/417; 544/212
[58] Field of Search ................ 524/100, 516, 521; 544/212; 525/186, 417

[56] References Cited

U.S. PATENT DOCUMENTS

| | | | |
|---|---|---|---|
| 4,028,334 | 6/1977 | Chalmers et al. | 524/100 |
| 4,086,204 | 4/1978 | Cassandrini et al. | 544/212 |
| 4,108,829 | 8/1978 | Cassandrini et al. | 544/212 |
| 4,250,268 | 2/1981 | Rody | 525/100 |
| 4,263,434 | 4/1981 | Cassandrini et al. | 544/212 |
| 4,294,963 | 10/1981 | Rody | 524/100 |
| 4,356,287 | 10/1982 | Loffelman et al. | 524/100 |
| 4,395,508 | 7/1983 | Nelli et al. | 525/186 |
| 4,400,505 | 8/1983 | Loffelman | 544/212 |
| 4,412,020 | 10/1983 | Loffelman et al. | 524/100 |
| 4,459,395 | 7/1984 | Cantatore | 524/100 |
| 4,491,643 | 1/1985 | Minagana et al. | 524/100 |
| 4,546,148 | 10/1985 | Cantatore | 525/186 |
| 4,547,548 | 10/1985 | Cantatore | 525/186 |

FOREIGN PATENT DOCUMENTS 2117377 10/1983 United Kingdom .

Primary Examiner—John Kight
Assistant Examiner—Kriellion Morgan
Attorney, Agent, or Firm—Wenderoth, Lind & Ponack

[57] ABSTRACT

Novel light stabilizers, heat stabilizers and oxidation stabilizers for synthetic polymers have been synthesized; these are of the formula:

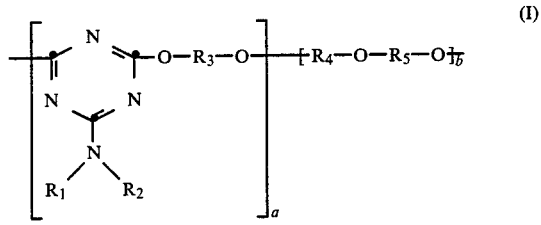

(I)

in which $R_3$ and $R_5$ can be identical or different and are radicals of formula (III), (IV), (V), (VI)

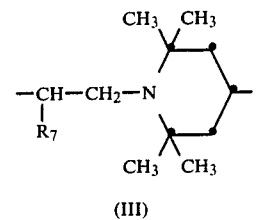

(III)

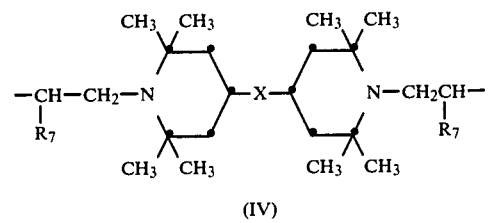

(IV)

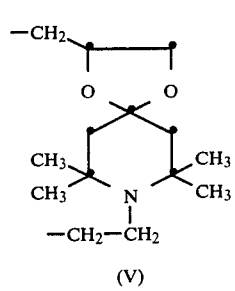

(V)

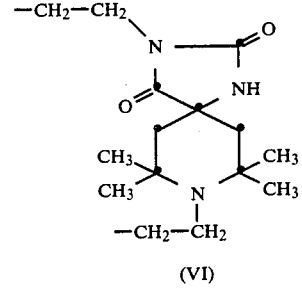

(VI)

and $R_5$ additionally can be a radical of formula VII

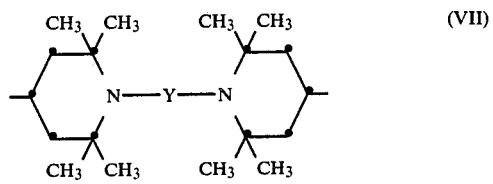

(VII)

and $R_4$ is $C_2$–$C_{18}$-diacyl or a radical of the formula

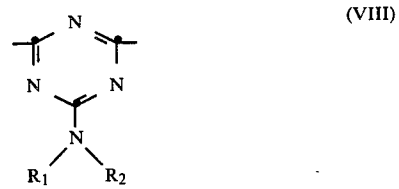

(VIII)

3 Claims, No Drawings

POLYMERIC COMPOUNDS CONTAINING PIPERIDINE RADICALS AND THEIR USE AS STABILIZERS FOR SYNTHETIC POLYMERS

The present invention relates to novel polymeric compounds which contain piperidine radicals and can be used as light stabilisers, heat stabilisers and oxidation stabilisers for synthetic polymers, and to the process for their preparation.

Hydroxyl groups containing polyethers carrying polyalkylpiperidylamino groups are disclosed in U.S. Pat. No. 4,294,963 as stabilizers for polymers. New triazine piperidylethers have now been found which show an outstanding effectiveness in improving the light stability of synthetic polymers.

In particular, the present invention relates to novel compounds of the formula

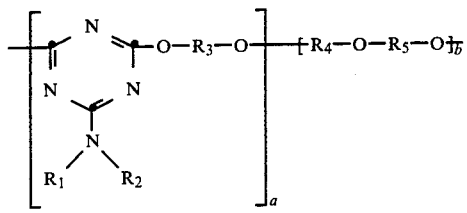

(I)

in which $R_1$ and $R_2$ can be identical or different and are hydrogen, $C_1$–$C_{18}$-alkyl, $C_2$–$C_{12}$-alkyl substituted by —OH, a $C_1$–$C_{18}$-alkoxy group or a $C_2$–$C_{18}$-dialkylamino group, $C_3$–$C_{18}$-alkenyl, $C_5$–$C_{18}$-cycloalkyl, $C_6$–$C_{18}$-aryl, $C_7$–$C_{18}$-aralkyl or a radical of the formula

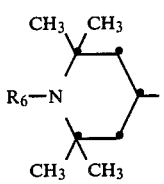

(II)

where $R_6$ is hydrogen, $C_1$–$C_{12}$-alkyl, $C_3$–$C_{12}$-alkenyl or -alkynyl, $C_7$–$C_{12}$-aralkyl or $C_1$–$C_{12}$-acyl, or $R_1$ and $R_2$, together with the nitrogen atom to which they are bonded, are a heterocyclic radical, such as pyrrolidin-1-yl, piperidin-1-yl, hexahydroazepin-1-yl, morpholin-4-yl or 4-methylpiperazin-1-yl, $R_3$ and $R_5$ can be identical or different and are radicals of the formula (III), (IV), (V) or (VI)

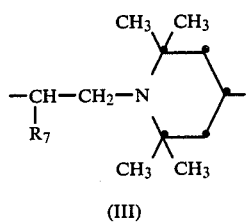

(III)

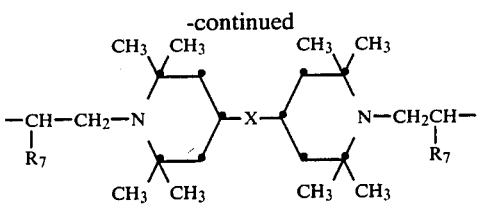

(IV)

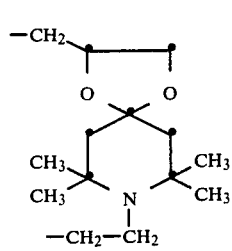

(V)

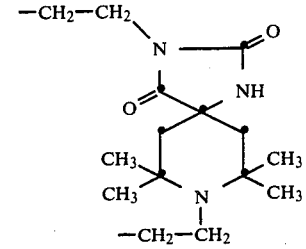

(VI)

and $R_5$ additionally can be a radical of formula VII

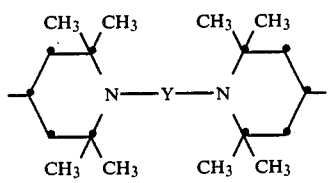

(VII)

wherein $R_7$ is hydrogen, $C_1$–$C_6$-alkyl or phenyl, X is a group —O—(CH$_2$)$_n$—O— or —N(R$_8$)—C(O)—(CH$_2$)$_n$—C(O)—N(R$_8$)—, n is a number between 1 and 6, $R_8$ has the same meaning as $R_1$ or $R_2$ and Y is $C_2$–$C_{12}$-alkylene, $C_3$–$C_{12}$-alkylene substituted by one hydroxyl or containing an oxygen atom in the chain, $C_4$–$C_{12}$-alkenylene or $C_8$–$C_{12}$-aralkylene, $R_4$ is $C_2$–$C_{18}$-diacyl or a radical of the formula (VIII)

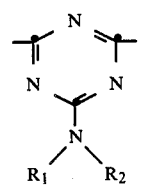

(VIII)

in which $R_1$ and $R_2$ are as defined above, a is a number between 0.2 and 1, and b is a number between zero and 0.8; the compounds of the formula (I) have a number average molecular weight $\overline{M}n$ between 1,000 and 20,000.

The meanings of the radicals present in the compounds of the formula (I) are:

for $R_1$, $R_2$ and $R_8$: hydrogen, methyl, ethyl, propyl, isopropyl, butyl, but-2-yl, isobutyl, hexyl, 2-ethylhexyl, octyl, decyl, dodecyl, hexadecyl, octadecyl, 2-hydroxyethyl, 3-hydroxypropyl, 2-methoxyethyl, 2-ethoxyethyl, 3-methoxpropyl, 3-ethoxypropyl, 3-octyloxypropyl, 3-dodecyloxypropyl, 3-octadecyloxypropyl, 3-dimethylaminopropyl, 3-diethylaminopropyl, 4-diethylaminobutyl, allyl, methallyl, but-2-enyl, undec-10-enyl, oleyl, cyclohexyl, methylcyclohexyl, trimethylcyclohexyl, cyclooctyl, cyclododecyl, phenyl, methylphenyl, dimethylphenyl, trimethylphenyl, t-butylphenyl, t-octylphenyl, methoxyphenyl, ethoxyphenyl, 3,5-di-t-butyl-4-hydroxyphenyl, benzyl, methylbenzyl, hydroxybenzyl, 3,5-di-t-butyl-4-hydroxybenzyl, 2,2,6,6-tetramethyl-piperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl and 1-acetyl-2,2,6,6-tetramethyl-piperidin-4-yl;

for $R_4$: oxalyl, malonyl, succinyl, glutaryl, adipoyl, sebacoyl, isophthaloyl, terephthaloyl or a radical of the formula (V) in which $R_1$ and $R_2$ have the preferred meanings defined above;

for $R_6$: hydrogen, methyl, ethyl, propyl, butyl, hexyl, octyl, decyl, dodecyl, allyl, methallyl, but-2-enyl, hex-2-enyl, propargyl, benzyl, methylbenzyl, t-butylbenzyl, hydroxybenzyl, acetyl, propionyl, butryl, caproyl and benzoyl;

for $R_7$: hydrogen, methyl, ethyl, -propyl, butyl, hexyl and phenyl, for Y: ethylene, trimethylene, tetramethylene, hexamethylene, octamethylene, decamethylene, dodecamethylene, 2-hydroxypropane-1,3-diyl, 3-oxapentane-1,5-diyl, but-2-ene-1,4-diyl and xylylene.

Compounds of the formula (I) which have given particularly interesting results are those in which $R_1$ and $R_2$ can be identical or different and are hydrogen, $C_1$–$C_{12}$-alkyl, $C_2$–$C_6$-alkyl substituted by $C_1$–$C_{12}$-alkoxy, $C_3$–$C_6$-alkenyl, $C_6$–$C_{10}$-cycloalkyl or a radical of the formula (II) in which $R_6$ is hydrogen, methyl, allyl, benzyl or acetyl, or the radicals $R_1$ and $R_2$, together with the nitrogen atom to which they are bonded, are a pyrrolidin-1-yl, piperidin-1-yl, hexahydroazepin-1-yl or morpholin-4-yl radical, $R_3$ and $R_5$ are a radical of formula (III) and $R_5$ additionally can be a radical of formula (VII), $R_7$ is hydrogen, methyl, or ethyl, Y is $C_2$–$C_6$-alkylene, but-2-ene-1,4-diyl or xylylene, $R_4$ is $C_2$–$C_{12}$-diacyl or a radical of the formula (VIII) in which $R_1$ and $R_2$ are as defined above, a is a number between 0.3 and 1, and b is a number between zero and 0.7, and the number average molecular weight $\overline{Mn}$ is between 1,500 and 10,000.

Compounds of the formula (I) which are preferred for the use according to the present invention are those in which $R_1$ and $R_2$ can be identical or different and are $C_1$–$C_8$-alkyl, cyclohexyl, 2,2,6,6-tetramethyl-piperidin-4-yl or 1,2,2,6,6-pentamethyl-piperidin-4-yl, $R_3$ and $R_5$ are a radical of formula (III) and $R_5$ additionally can be a radical of formula (VII), $R_7$ is hydrogen or methyl, Y is but-2-ene-1,4-diyl or xylylene, a is 1 and b is zero, and the number average molecular weight $\overline{Mn}$ is between 1,500 and 6,000.

If b is other than zero, the compounds of the formula (I) can be prepared by reacting a mixture of the compounds of the formula (IX) and (X)

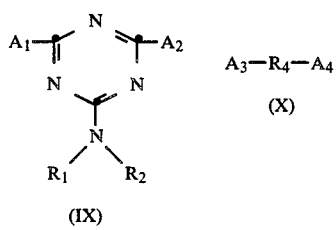

in which $R_1$, $R_2$ and $R_4$ are as defined above and $A_1$, $A_2$, $A_3$ and $A_4$ are Cl or $C_1$–$C_4$-alkoxy, with a compound of formula (XI), (XII), (XIII) or (XIV)

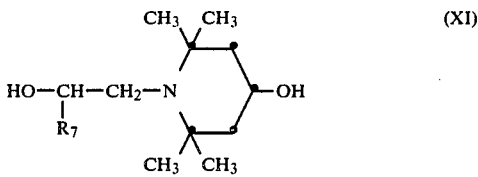

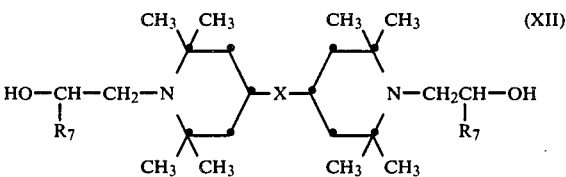

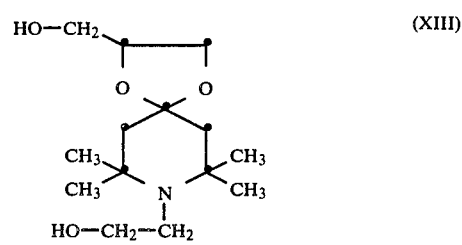

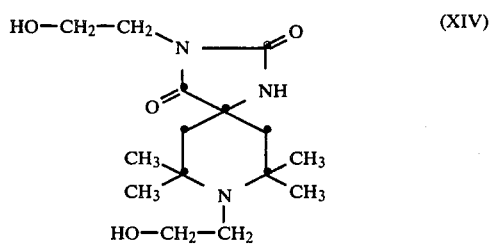

and, if $R_5$ is a radical of formula VII, additionally with a compound of formula XV

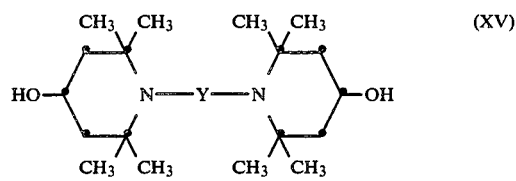

wherein $R_7$, X and Y are as defined above, preferably in a stoichiometric ratio.

If b is zero, the compounds of the formula (I) are prepared by reacting a compound of the formula (IX) with a compound of formula (XI), (XII), (XIII) or (XIV) and optionally (XV) in an approximately stoichiometric ratio.

In both cases, the reaction can be effected in the presence or absence of an inert organic solvent and in the presence of an organic or inorganic base, if $A_1$, $A_2$, $A_3$ and 4 are Cl, or in the presence of a transesterification catalyst, if $A_1$, $A_2$, $A_3$ and $A_4$ are alkoxy groups.

Inert organic solvents suitable for use as reaction media are, for example, benzene, toluene, xylene, ethylbenzene, trimethylbenzene, tetralin, decalin, octane, decane, mixtures of aliphatic hydrocarbons having boiling points between 100° and 200° C., dioxane, dibutyl ether, 1,2-dimethoxyethane, 1,2-diethoxyethane, diethylene glycol dimethyl ether and diethylene glycol diethyl ether.

To fix the hydrochloric acid liberated in the process, if reagents are used in which $A_1$, $A_2$, $A_3$ and $A_4$ are Cl, suitable organic and inorganic bases are, for example, pyridine, triethylamine, tributylamine, sodium hydroxide, potassium hydroxide, sodium carbonate or potassium carbonate; in every case the base is used in a quantity almost equivalent to the hydrohalic acid liberated in the reaction.

In the case where $A_1$, $A_2$, $A_3$ and $A_4$ are alkoxy groups, examples of transesterification catalysts which can be used are alkali metals and alcoholates, hydrides and amides of alkali metals.

The polycondensation reactions can be effected at temperatures between 80° and 280° C., preferably betwen 100° and 200°, in a molar ratio (compound of the formula (IX)+compound of the formula (X): (compound of the formula (XI), (XII), (XIII) or (XIV)- +compound of the formula (XV) of between 1.3:1 and 1:1.3, preferably between 1.2:1 and 1:1.2.

The various reagents can be introduced into the reaction simultaneously or in successive phases.

The compounds of the formula (IX) can be obtained by known processes, starting from cyanuric chloride; the dichloro-triazines or dialkoxy-triazines prepared can be employed directly without isolation in the reaction mixture, or after isolation. The compounds of formula (XI), (XII), (XIII), (XIV) and (XV) are known compounds.

In order to illustrate the present invention more clearly, several examples of the preparation of compounds of the formula (I) are described below; these examples are given by way of illustration only and do not imply any restriction.

EXAMPLE 1

35.1 g (0.1 mole) of 2-[N-(2,2,6,6-tetramethylpiperidin-4-yl)-butylamino]-4,6-dimethoxy-1,3,5-triazine, 20.1 g (0.1 mole) of 1-(2-hydroxyethyl)-2,2,6,6-tetramethyl-piperidin-4-ol, 0.3 g of sodium hydride and 200 ml of xylene are heated under reflux for 12 hours, the solvent being slowly distilled off, together with the methanol liberated during the reaction, and being replaced with an equal volume of fresh solvent.

The reaction mixture is evaporated to dryness and the residue obtained is ground, washed with water and dried.

The product obtained has a melting point of 205°–215° C. and a number average molecular weight $\overline{M}n$ of 4,300.

EXAMPLES 2 AND 3

The procedure described in Example 1 is repeated for the preparation of other compounds of the formula (I) from the reagents specified below and in the indicated ratios.

| Example | Reagents | | Product $\overline{M}n$ | melting point |
|---|---|---|---|---|
| 2 | (CH₃O-triazine-OCH₃ with N-(CH₂)₃-OC₂H₅ substituted tetramethylpiperidine) 38.1 g (0.1 m) | HOCH₂CH₂N-(tetramethylpiperidin-4-ol) 20.1 g (0.1 m) | 3200 | 160–172° C. |
| 3 | (CH₃O-triazine-OCH₃ with N(C₂H₅)₂) 21.2 g (0.1 m) | HOCH₂CH₂N-(tetramethylpiperidin-4-ol) 20.1 g (0.1 m) | 1800 | 152–160° C. |

EXAMPLE 4

26,8 g (0.1 mole) of 4-octylamino-2,2,6,6-tetramethyl-piperidine are added slowly, while not exceeding 10° C., to a solution of 18.5 g (0.1 mole) of cyanuric chloride in 180 ml of trimethylbenzene, cooled to 0° C.

A solution of 4 g of sodium hydroxide in 50 ml of water is then added, while maintaining the temperature at 10° C.

To the mixture thus obtained, 20.1 g (0.1 mole) of 1-(2-hydroxyethyl)-2,2,6,6-teramethyl-piperidin-4-ol and 12 g of sodium hydroxide are added, and the mixture is heated under reflux for 20 hours with azeotropic removal of the water.

After filtration, in order to separate off the inorganic products, and after removal of the solvent, a product is obtained which melts at 145°–152° C. and has a number average molecular weight $\overline{M}n$ of 2200.

EXAMPLES 5-6

The procedure in Example 4 is repeated for the preparation of two further compounds of the formula (I) from the reagents specified below and in the indicated ratios:

| Example | Reagents | | | Product $\overline{M}n$ | melting point |
|---|---|---|---|---|---|
| 5 | 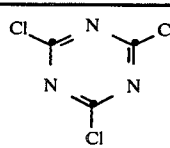 18,5 g (0.1 m) | 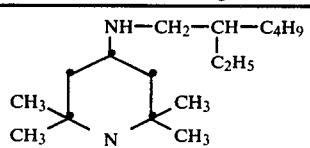 26,8 g (0.1 m) | 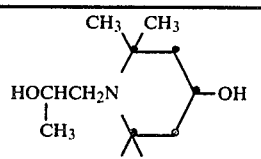 21,4 g (0.1 m) | 1600 | 125–136° C. |
| 6 | 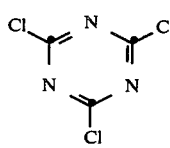 18,5 g (0.1 m) | 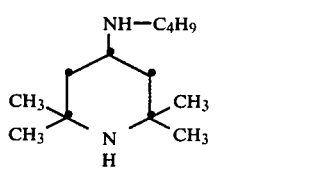 21,2 g (0.1 m) | 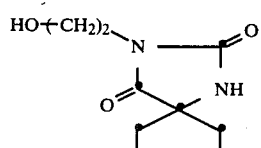 31,2 g (0.1 m) | 2450 | 210–220° C. |

EXAMPLE 7

20.4 g (0.05 mole) of 2,4-dimethoxy-6-[N-(2,2,6,6-tetramethyl-piperidin-4-yl)-octylamino]-1,3,5-triazine, and 20.1 g (0.1 mole) of 1-(2-hydroxyethyl)-2,2,6,6-tetramethylpiperidin-4-ol, 0.25 g of sodium and 200 ml of xylene are heated under reflux for 8 hours, the solvent being distilled off, together with the methanol produced during the reaction, and being replaced by an equal volume of fresh xylene.

The mixture is cooled to 80° C., and 7.3 g (0.05 mole) of dimethyl succinate are added, and the mixture is heated under reflux for a further 8 hours with continuing replacement of the solvent.

After the end of the reaction, the mixture is diluted with 200 ml of xylene and filtered, and the filtrate is evaporated to dryness. The product obtained melts at 95°–103° C. and has a number average molecular weight $\overline{M}n$ of 3,700.

EXAMPLE 8

Using the same procedure as that described in Example 7, a copolymer is prepared, using 17.55 g (0.05 mole) of 2-[N-(2,2,6,6-tetramethyl-piperidin-4-yl)-butylamino]-4,6-dimethoxy-1,3,5-triazine, 20.1 g (0.1 mole) of 1-(2-hydroxyethyl)-2,2,6,6-tetramethylpiperidin-4-ol and 7.3 g (0.05 mole) of dimethyl succinate as the reagents.

The product obtained melts at 125°–134° C. and has a number average molecular weight $\overline{M}n$ of 2,000.

As mentioned at the outset, the compounds of the formula (I) are very effective in improving the light stability, heat stability and oxidation stability of synthetic polymers, for example high-density and low-density polyethylene, polypropylene, ethylene/propylene copolymers, ethylene vinyl acetate copolymers, poylbutadiene, polyisoprene, polystyrene, butadiene/styrene copolymers, vinyl chloride/vinylidene chloride polymers and copolymers, polyoxymethylene, polyurethanes, saturated and unsaturated polyesters, polyamides, polycarbonates, polyacrylates, alkyd resins and epoxide resins.

The compounds of the formula (I) can be mixed with the synthetic polymers in various proportions depending on the nature of the polymer, and end use and the presence of other additives. In general, it is advantageous to employ from 0.01 to 5% by weight of the compounds of the formula (I), relative to the weight of the polymers, preferably from 0.05 to 1%.

The compounds of the formula (I) can be incorporated into the polymeric materials by various processes, such as dry blending in the form of powders, or wet mixing in the form of solutions or suspensions, or mixing in the form of a masterbatch; in these operations, the synthetic polymer can be employed in the form of powder, granules, a solution, a suspension or in the form of a latex.

The polymers stabilised with the products of the formula (I) can be used for the preparation of moulded articles, films, tapes, fibres, monofilaments, surface-coatings and the like.

If desired, other additives, such as antioxidants, ultraviolet absorbers, nickel stabilisers, pigments, fillers, plasticizers, antistatic agents, flameproofing agents, lubricants, anti-corrosion agents and metal deactivators, can be added to the mixtures of the compounds of the formula (I) with the synthetic polymers.

Examples of additives which can be mixed with the compounds of the formula (I) are, in particular:

1. Antioxidants 1.1. Alkylated monophenols, for example,
    2,6-di-tert.butyl-4-methylphenol
    2-tert.butyl-4,6-dimethylphenol
    2,6-di-tert.butyl-4-ethylphenol
    2,6-di-tert.butyl-4-n-butylphenol
    2,6-di-tert.butyl-4-i-butylphenol
    2,6-di-cyclopentyl-4-methylphenol
    2-(α-methylcyclohexyl)-4,6-dimethylphenol
    2,6-di-octadecyl-4-methylphenol
    2,4,6-tri-cyclohexylphenol
    2,6-di-tert.butyl-4-methoxymethylphenol 1.2. Alkylated hydroquinones, for example,
    2,6-di-tert.butyl-4-methoxyphenol
    2,5-di-tert.-hydroquinone
    2,5-di-tert.amyl-hydroquinone
    2,6-diphenyl-4-octadecyloxyphenol 1.3. Hydroxylated thiodiphenyl ethers, for example
    2,2'-thio-bis-(6-tert.butyl-4-methylphenol)
    2,2'-thio-bis-(4-octylphenol)
    4,4'-thio-bis-(6-tert.butyl-3-methylphenol)
    4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonyl-phenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.butyl-4-methylphenyl]-terephthalate.

1.5. Benzylcompounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid-isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamidate 1.7. Esters of β-(3,5-di-tert.butyl-4-hydroxyphenyl)-propionic acid with monohydric or polyhydric alcohols, for example,
methanol
octadecanol
1,6-hexanediol
neopentylglycol
thiodiethyleneglycol
diethyleneglycol
triethyleneglycol
pentaerytritol
tris-hydroxyethyl isocyanurate
di-hydroxyethyl oxalic acid diamide 1.8. Ester of β-(5-tert.butyl-4-hydroxy-3-methylphenyl)propionic acid with monohydric or polyhydric alcohols, for example,
methanol
octadecanol
1,6-hexanediol
neopentylglycol
thiodiethyleneglycol
diethyleneglycol
triethyleneglycol
pentaerytritol
tris-hydroxyethyl isocyanurate
di-hyroxyethyl oxalic acid
diamide 1.9. Amides of β-(3,5-di-tert.butyl-4-hydroxyphenyl)-propionic acid for example,
N,N'-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy-, 3',5'-di-tert.amyl-, 3',5'-bis-(α,α-dimethylbenzyl)-derivative. 2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythrit diphosphite, tris-(2,4-di-tert.butylphenyl)-phosphite, di-isodecylpentaerythrit diphosphite, di-(2,4-di-tert.butylphenyl)pentaerythrit diphosphite, tristearyl-sorbite triphosphite, tetrakis-(2,4-di-tert.butylphenyl)-4,4'-biphenylylen diphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrit-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flame-proofing agents, antistatic agents and blowing agents.

The efficiency, as stabilisers, of the products prepared according to the present invention is illustrated in the examples which follow, in which the same products obtained in the preparation examples are used for stabilising polypropylene tapes and fibres.

EXAMPLE 9

2 g of each of the products indicated in Table 1, 1 g of pentaerythritol tetrakis-3-(3,5-di-t-butyl-4-hydroxyphenyl)propionate and 1 g of calcium stearate are mixed, in a powder mixer, with 1,000 g of polypropylene powder of melt index 2.4 (® Propathene HF 18, a product of Imperial Chemical Industries).

The mixtures obtained are extruded at a temperature of 180°–220° C., to give polymer granules which are then converted into stretched tapes of 50 μm thickness and 2.5 mm width, under the following working conditions:
extruder temperature: 220°–240° C.
head temperature: 240° C.
stretch ratio: 1:6.

The tapes thus prepared are exposed, mounted on a white card, in a Weather-Ometer 65 WR model (ASTM G 27–70), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

For comparison, polypropylene tapes prepared under the same conditions as indicated above, but without the addition of the compounds of the invention, are exposed.

The results obtained are shown in Table 1:

TABLE 1

| Stabiliser | $T_{50}$ (hours) |
|---|---|
| None | 240 |
| Compound of Example 4 | 2,370 |
| Compound of Example 5 | 1,600 |
| Compound of Example 7 | 1,800 |

EXAMPLE 10

2.5 g of each of the products indicated in Table 2, 1 g of octadecyl 3-(3,5-di-t-butyl-4-hydroxyphenyl)-propionate, 1 g of calcium stearate and 2.5 g of titanium dioxide (® KRONOS RN 57) are mixed, in a powder mixer, with 1,000 g of polypropylene powder of melt index 13 (® Propathene HF 85, a product of Imperial Chemical Industries).

The mixtures are extruded at 180°–220° C., to give polymer granules which are then converted into fibres, under the following working conditions:
extruder temperature: 220°–240° C.
spinneret temperature: 240° C.
stretch ratio: 1:3.5
count: 20 deniers per fibre.

The fibres thus obtained are exposed, mounted on a white card, in a Weather-Ometer 65 WR model with a black panel temperature of 63° C.

The $T_{50}$ value as described in the preceding example is then calculated.

For comparison, the data obtained with fibres prepared under the same conditions as described above, but without the addition of the compounds of the invention, are also given.

The results obtained are shown in Table 2:

TABLE 2

| Stabiliser | $T_{50}$ (hours) |
|---|---|
| None | 120 |
| Compound of Example 4 | 1,070 |
| Compound of Example 5 | 1,110 |
| Compound of Example 7 | 1,050 |
| Compound of Example 8 | 1,370 |

The data reported above clearly show the stabilising effect obtained with the novel products according to the present invention.

What is claimed is:

1. A light-stabilized, heat-stabilized and oxidation-stabilized polymer composition comprising a synthetic polymer and one or more stabilizers of the formula (I),

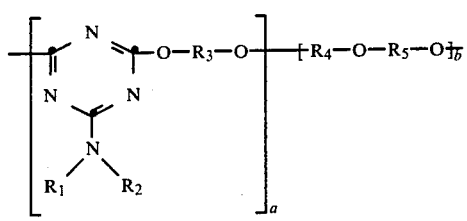 (I)

in which $R_1$ and $R_2$ can be identical or different and are (1) hydrogen, (2) $C_1$–$C_{18}$-alkyl, (3) $C_2$–$C_{12}$-alkyl substituted by —OH, a $C_1$–$C_{18}$-alkoxy group or a $C_2$–$C_{18}$-dialkylamino group, (4) $C_3$–$C_{18}$-alkenyl, (5) $C_5$–$C_{18}$-cycloalkyl, (6) $C_6$–$C_{18}$-aryl, (7) $C_7$–$C_{18}$-aralkyl or (8) a radical of the formula

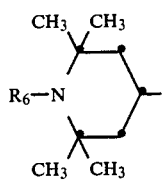 (II)

where $R_6$ is hydrogen, $C_1$–$C_{12}$-alkyl, $C_3$–$C_{12}$-alkenyl or -alkynyl, $C_7$–$C_{12}$-aralkyl or $C_1$–$C_{12}$-acyl, or $R_1$ and $R_2$, together with the nitrogen atom to which they are bonded, are a heterocyclic radical, such as pyrrolidin-1-yl, piperidin-1-yl, hexahydroazepin-1-yl, morpholin-4-yl or 4-methylpiperazin-1-yl, $R_3$ and $R_5$ can be identical or different and are radicals of the formula (III), (IV), (V) or (VI)

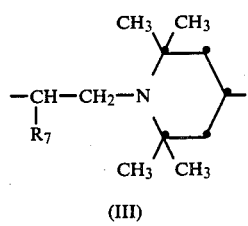

(III)

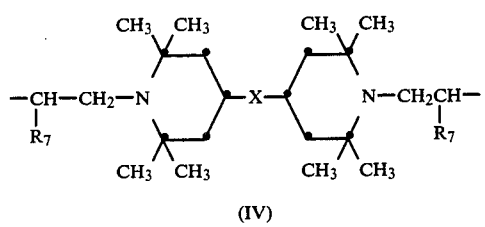

(IV)

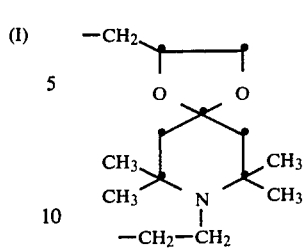 (V)

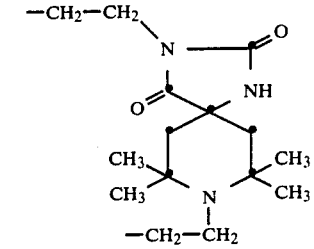 (VI)

and $R_5$ additionally can be a radical of formula VII

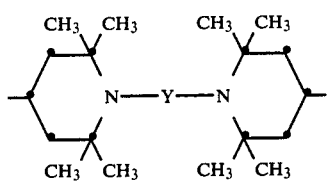 (VII)

wherein $R_7$ is hydrogen, $C_1$–$C_6$-alkyl or phenyl, X is a group —O—(CH$_2$)$_n$O— or —N(R$_8$)—C(O)—(CH$_2$)$_n$-C(O)—N(R$_8$)—, n is a number between 1 and 6, $R_8$ has the same meaning as $R_1$ or $R_2$ and Y is $C_2$–$C_{12}$-alkylene, $C_3$–$C_{12}$-alkylene substituted by one hydroxyl or containing an oxygen atom in the chain, $C_4$–$C_{12}$-alkenylene or $C_8$–$C_{12}$-aralkylene, $R_4$ is $C_2$–$C_{18}$-diacyl or a radical of the formula (VIII)

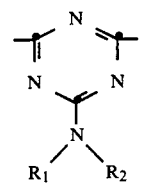 (VIII)

in which $R_1$ and $R_2$ are as defined above, a is a number between 0.2 and 1, and b is a number between zero and 0.8; and the compounds of the formula (I) have a number average molecular weight $\overline{Mn}$ between 1,000 and 20,000, said compound(s) of formula (I) being present in a quantity from 0.01 to 5% by weight, relative to the weight of the synthetic polymer which is selected from the group consisting of high-density and low-density polyethylene, polypropylene, ethylene/propylene copolymers, ethylene vinyl acetate copolymers, polybutadiene, polyisoprene, polystyrene, butadiene/styrene copolymers, vinyl chloride/vinylidene chloride polymers and copolymers, polyoxymethylene, polyurethanes, saturated and unsaturated polyesters, polyamides, polycarbonates, polyacrylates, alkyd resins and epoxide resins.

2. A composition according to claim 1, which, in addition to the stabiliser of the formula (I) contains other conventional additives for synthetic polymers.

3. A composition according to claim 1, wherein the synthetic polymer is polyethylene or polpropylene.

* * * * *